(12) United States Patent
Celli et al.

(10) Patent No.: US 7,833,254 B2
(45) Date of Patent: Nov. 16, 2010

(54) DEVICE FOR THE OSTHEOSYNTHESIS OF PROXIMAL HUMERUS FRACTURES

(75) Inventors: Luigi Celli, Carpi (IT); Andrea Celli, Carpi (IT); Daniele Venturini, Povegliano Veronese (IT); Luigi Rossi, Peschiera del Garda (IT); Rudj Bardini, Monzambano (IT)

(73) Assignee: Orthofix International B.V., Amsterdam (NL)

( * ) Notice: Subject to any disclaimer, the term of this patent is extended or adjusted under 35 U.S.C. 154(b) by 1286 days.

(21) Appl. No.: 11/372,746

(22) Filed: Mar. 10, 2006

(65) Prior Publication Data
US 2006/0235402 A1    Oct. 19, 2006

(30) Foreign Application Priority Data
Mar. 11, 2005   (EP)   ................................. 05425144

(51) Int. Cl.
*A61B 17/80* (2006.01)
(52) U.S. Cl. .................. 606/295; 606/289; 606/286; 606/290
(58) Field of Classification Search ............. 606/64–68, 606/70–71, 280–299, 311
See application file for complete search history.

(56) References Cited

U.S. PATENT DOCUMENTS

| | | | | |
|---|---|---|---|---|
| 3,842,825 A | * | 10/1974 | Wagner | 606/66 |
| 4,791,918 A | * | 12/1988 | Von Hasselbach | 606/65 |
| 5,127,914 A | * | 7/1992 | Calderale et al. | 606/65 |
| 5,129,901 A | * | 7/1992 | Decoste | 606/65 |
| 5,514,138 A | * | 5/1996 | McCarthy | 606/65 |
| 5,665,089 A | * | 9/1997 | Dall et al. | 606/71 |
| 5,749,872 A | * | 5/1998 | Kyle et al. | 606/66 |
| 6,096,040 A | | 8/2000 | Esser | |
| 6,235,033 B1 | * | 5/2001 | Brace et al. | 606/288 |
| 6,468,278 B1 | * | 10/2002 | Muckter | 606/291 |
| 7,207,993 B1 | * | 4/2007 | Baldwin et al. | 606/70 |
| 7,670,341 B2 | * | 3/2010 | Leyden et al. | 606/65 |
| 2004/0167522 A1 | | 8/2004 | Niederberger et al. | |
| 2004/0225291 A1 | * | 11/2004 | Schwammberger et al. | 606/71 |
| 2004/0254579 A1 | * | 12/2004 | Buhren et al. | 606/71 |
| 2004/0260295 A1 | | 12/2004 | Orbay et al. | |
| 2005/0049594 A1 | | 3/2005 | Wack et al. | |
| 2005/0101959 A1 | * | 5/2005 | Mitkovic | 606/69 |
| 2005/0182406 A1 | * | 8/2005 | Orbay et al. | 606/69 |
| 2005/0234457 A1 | * | 10/2005 | James et al. | 606/69 |
| 2006/0155282 A1 | * | 7/2006 | Vese | 606/69 |
| 2006/0241606 A1 | * | 10/2006 | Vachtenberg et al. | 606/65 |
| 2009/0287215 A1 | * | 11/2009 | Fisher et al. | 606/71 |

* cited by examiner

FOREIGN PATENT DOCUMENTS

FR         2501033       9/1982

*Primary Examiner*—Eduardo C Robert
*Assistant Examiner*—Jan Christopher Merene
(74) *Attorney, Agent, or Firm*—Seed IP Law Group PLLC (57) ABSTRACT

A device for use in the treatment of proximal humerus fractures, comprising a substantially spoon-shaped body having a blade-like proximal portion intended to complement the humerus head and provided with at least one seat in which to insert a wire, a threaded nail, or a similar element to stabilize the fracture, a plate-like and elongate distal portion, intended to complement the humerus neck and provided with at least one seat in which to insert a screw or a similar element to fix the body to the humerus, and a central bulge, or block, interposed between the proximal portion and the distal portion and wherein a seat is obtained in which to insert a screw intended to stabilize the humerus head.

23 Claims, 6 Drawing Sheets

DEVICE FOR THE OSTHEOSYNTHESIS OF PROXIMAL HUMERUS FRACTURES

BACKGROUND OF THE INVENTION

1. Field of the Invention

The present invention generally relates to a device for the treatment (ostheosynthesis) of proximal humerus fractures, i.e., of the humerus head and neck, to mend and fix in the correct position fractures having one or more fragments.

The device is particularly suitable for the treatment of the proximal humerus fractures of the III or V type according to the Neer classification.

The device generally comprises a body, or plate being substantially spoon-shaped, i.e., comprising a blade-like proximal portion intended to match the humerus head and provided with at least one seat to insert a threaded wire, a nail, or a similar element to stabilize the fracture, and a plate-like distal portion, having an elongate shape, intended to match the humerus neck and provided with at least one seat to insert a screw or similar element to fix the body to the humerus.

2. Description of the Related Art

As it is well known in the field, the humerus, and particularly the proximal portion thereof comprising the head and the neck, is considered as a fragile bone, particularly subject to fractures, mainly in people affected by osteoporosis.

Generally these fractures involve the formation of a plurality of fragments and fissures having different features from each other, substantially depending on the bone composing structure, the patient's age and the trauma type.

To compact the plurality of fragments and allow the ostheosynthesis thereof, the use of a plate being substantially spoon-shaped is widespread since a long time, which has a uniform and relatively reduced thickness of about 1-2 mm to tenderly match the proximal humerus, and particularly on the periosteous membrane thereof.

The plate comprises a blade-like proximal portion, wherein one or more seats are obtained to insert nails or threaded wires and a plate-like elongate distal portion wherein one or more seats are obtained to insert fixing screws.

Once mounted, the distal portion fits in the humerus neck and it is fixed therein by means of fixing screws, while the proximal portion fits in the humerus head below the big tubercle.

Afterwards, according to the occurred fracture, one or more threaded wires or nails are inserted in the corresponding proximal portion seats, penetrating the humerus head to make a structure compressing the bone fragments therein.

The threaded wire location and orientation depend on the type of fracture being occurred.

Known devices, although responding to the scope of allowing the ostheosynthesis, have however known still-unsolved drawbacks.

The main drawback is that the humerus scheletric tissue, mainly in case of heavy osteoporosis, undergoes a bone mass loss, especially of the spongious bone mass, with a considerable consistency reduction. A risk of loss of stability of the structure formed by the wires inserted in the humerus head and, consequently, also an insufficient fragment stability result therefrom, with a loss of resistance to physiological as well as traumatic stresses.

This involves the risk that the plate, because of the stresses undergone by the bone, tends to lose the adhesion with the humerus, determining a progressive weakening of the fixing thereof. A period revision of the plate functionality, or eventually a replacement thereof, is thus necessary.

The technical problem underlying the present invention is thus to provide a device for the ostheosynthesis of proximal humerus fractures overcoming the above-mentioned drawbacks of known devices so as to ensure a plate greater application stability in time.

BRIEF SUMMARY OF THE INVENTION

This technical problem is solved by a device as mentioned above comprising, according to the invention, a central bulge, or block, interposed between the proximal portion and the distal portion and wherein a seat is obtained to insert a screw intended to stabilize the humerus head.

Further features and advantages of the device according to the invention will be more apparent from the following description of an embodiment thereof given by way of non-limiting example with reference to the attached drawings.

DETAILED DESCRIPTION OF THE INVENTION

Figure 1:
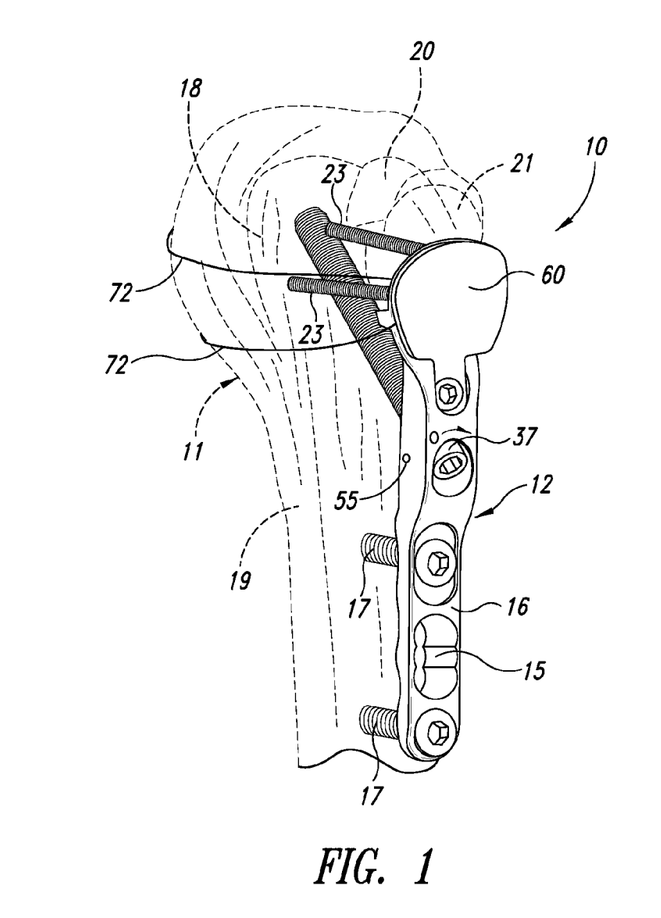
FIG. 1 shows a device according to one embodiment of the invention for the fracture ostheosynthesis applied on a right humerus.

With reference to the attached drawings, with the reference number 10 it is generally indicated a device according to the present invention for the treatment of fractures of the proximal humerus 11. The latter is schematically shown in FIG. 1 by a dotted line and in FIG. 2 by a continuous line.

The device 10 comprises a body 12, commonly called a plate, having an overall spoon shape, i.e., comprising a blade-like proximal portion 14 and an elongate plate-like distal portion 16.

The body 12 has, in the case of the solution being shown, a length L (FIG. 7A) of about 9 cm and it is preferably made of titanium, although other suitable sizes and materials may be used.

The proximal portion 14, also called head portion, is suitable to match the head 20 of the humerus 11, and more precisely the periosteous membrane, preferably behind the bicipital groove 18, on a plane whereon the rotation center of the humerus head 20 lies, and below the big tubercle 21.

Figure 8:
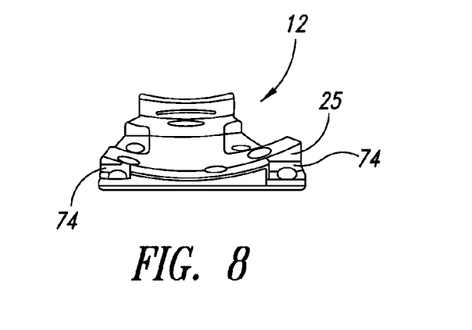
FIG. 8 shows a view from above of the body of FIG. 5.

In the case of the solution being shown, the proximal portion 14 is containment-basket-shaped and particularly it has a slightly concave shape (FIG. 8), with the concavity turned towards the humerus 11, to adhere with the humerus head 20 shape and contain bone fragments.

The proximal portion 14 comprises one or more seats 32 (FIGS. 2, 5 and 6) to insert threaded wires 23, nails or similar elements to stabilize the humerus 11 fracture. In the case being shown, the threaded wires 23 have a stem 23a that can be easily broken once the threaded wires 23 are inserted in the humerus head 20.

In the case of the solution being shown, there are four of the seats 32 and they are positioned in a substantially triangular configuration. Therefore threaded wires 23, once inserted in the humerus head 20, form a triangular assembly. Further details about the proximal portion 14 and seats 32 will be described hereafter.

The distal portion 16 is suitable to match the humerus neck 19 and it has one or more seats 15 for the insertion of fixing screws 17 to fix the whole body 12 to the humerus 11.

In the case of the solution being shown, there are three of the seats 15 for the fixing screws 17. In this case too, further details about the distal portion 16 and seats 15 will be described hereafter.

According to the invention, the device 10 comprises a central bulge 35 (FIG. 3), or block, which is interposed between the proximal portion 14 and the distal portion 16.

Figure 7:
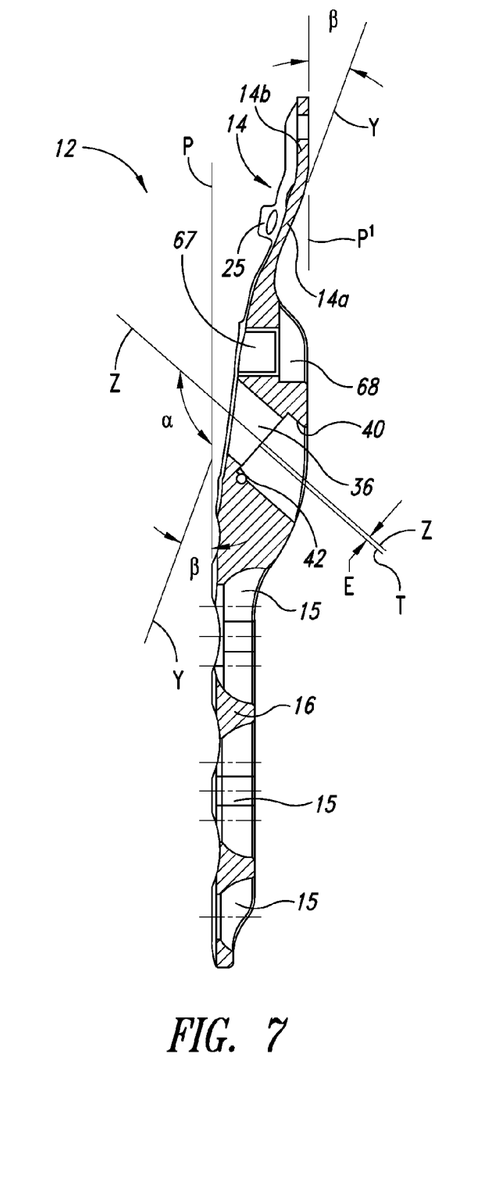
FIG. 7 shows a view of a section according to the line VII-VII of the body of FIG. 5.
Figure 7A:
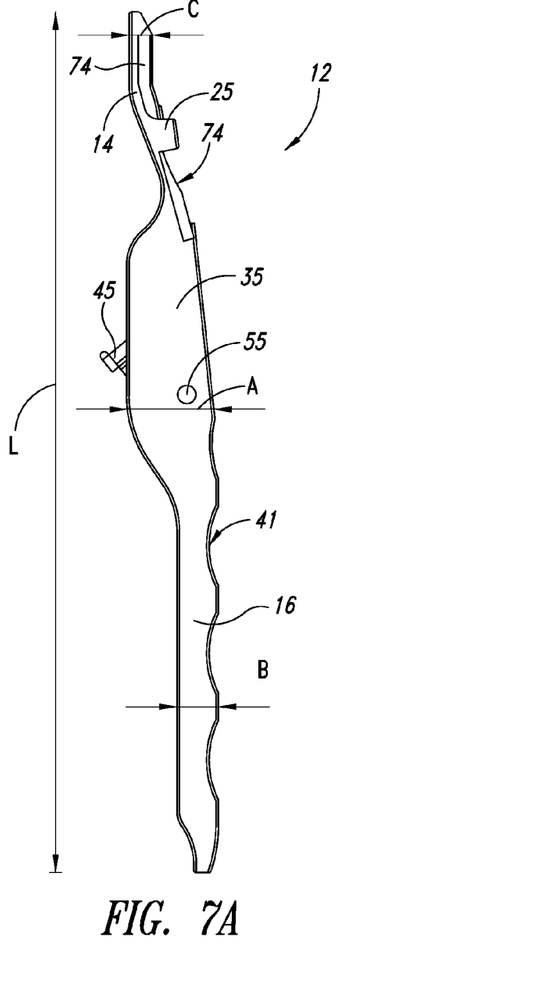
FIG. 7a shows a side view of the body of FIG. 5.

In practice, according to the invention, the device 10 comprises, besides the proximal portion 14 and the distal portion 16, a three-dimensional central block 35, forming the central portion of the body 12 and having, as it can be clearly seen in the attached drawings, a thickness A being considerably higher than the thickness C of the proximal portion 14 and the thickness B of the distal portion 16 (FIG. 7A).

Figure 9:
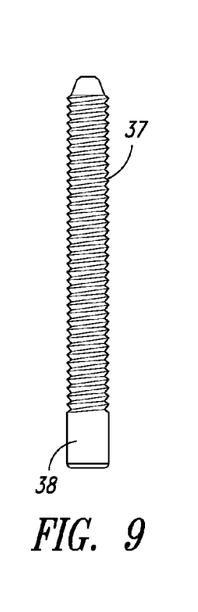
FIG. 9 shows a view of a screw for the humerus head stabilization according to the invention.

The bulge 35 comprises, according to the present invention, a seat 36 for the insertion of a screw 37 (FIGS. 2 and 9) intended to make a main stabilization of the humerus head 20.

For convenience of illustration, in the following description this main stabilizing screw is called cephalic screw 37. The cephalic screw 37 serves to realize a stiff structure being fixed to the body 12 allowing a stable-in-time positioning of threaded wires 23 to be obtained.

In the case of the solution being shown, the cephalic screw 37 has a smooth head portion 38 (FIG. 9) conveniently sized to be inserted by pressure in the seat 36 once the cephalic screw 37 is screwed down in the bone.

The seat 36 shapes up in a through hole obtained in the bulge 35 and having an axis Z (FIG. 7). In particular, the axis Z forms an angle (angle α) with a vertical plane P comprised between about 120° and 135°, preferably about 130°.

The vertical plane P substantially corresponds to a plane whereon the distal portion 16 lies and substantially coinciding with an ideal supporting plane of the distal portion 16 on the humerus neck 19.

Preferably, according to another feature of the invention, the thickness of the bulge 35 is coherently chosen according to the size of the cephalic screw 37 to obtain a uniformly solid structure, comprising the body 12 and the cephalic screw 37.

In the case of the solution being shown, the bulge 35 has an overall or highest thickness A comprised between about 9 and 11 mm (0.35"-0.43"), preferably 10 mm (0.39"), while the distal portion 16 has an overall or highest thickness B comprised between about 4 and 5 mm (0.16'-0.20"), preferably about 4.5 mm (0.18") and the proximal portion 14 an overall or highest thickness C comprised between 0.9 and 1.5 mm (0.03"-0.06"), preferably 1.1 mm (0.04").

The cephalic screw 37 has a diameter preferably comprised between 5 and 7 mm (0.20"-0.27"), preferably about 6 mm (0.24"), moreover it is slightly conic and self-drilling.

Figure 10:
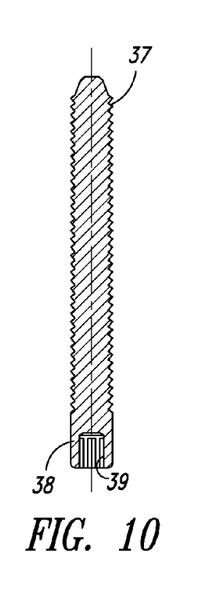
FIG. 10 shows a section of the screw of FIG. 9.

Moreover the cephalic screw 37 is cannulated (FIG. 10) to allow a guide wire, such as a Kirshner wire, to be inserted, suitable to be inserted in advance in the bone to control the position of the cephalic screw 37. Moreover a hexagonal embedded seat 39 (FIG. 10) is obtained in the head portion 38 of the screw 37 to screw down the screw 37 by means of a convenient tool 24, such as for example the one shown in FIG. 19.

Figure 5:
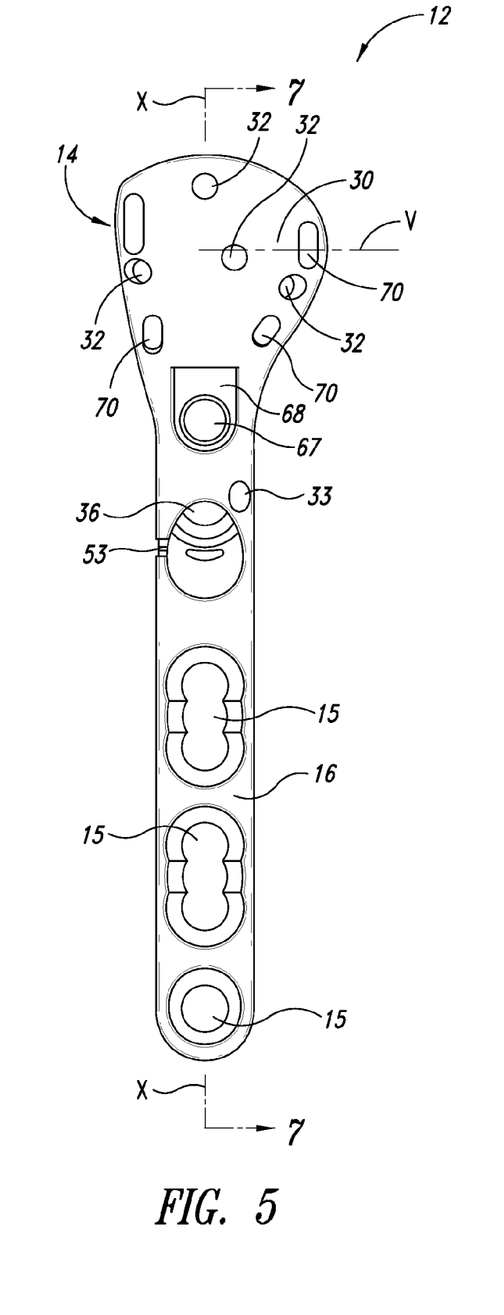
FIG. 5 shows a front view of a body, or plate, of the device of FIG. 3 for the left humerus.
Figure 6:
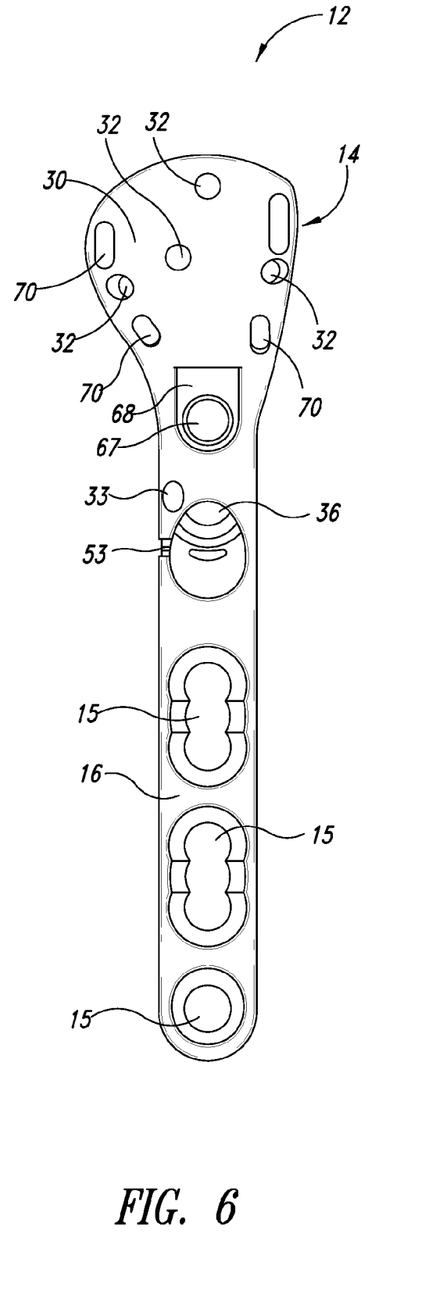
FIG. 6 shows a front view of a body, or plate, of the device of FIG. 4 for the right humerus.

With reference to FIGS. 5 and 6, it is possible to observe that a further hole 33 is obtained near the seat 36 for a Kirshner guide wire to guide the positioning of the body 12 on the humerus 11.

According to an alternative embodiment not being shown, the body 12 is completed by a plurality of holes positioned along the whole body 12 for the insertion of corresponding guide wires.

Preferably, the cephalic screw 37 is firmly constrained to the bulge 35 by means of a corresponding clamping system nearly to form a unique piece with the bulge 35 in order to reduce the compression of the whole device on the periosteous membrane.

In the case of the solution being shown, the clamping system being used is an eccentric system comprising a substantially cylindrical counterbore 40 (FIG. 7) being obtained in the bulge 35 around the insertion seat 36 of the cephalic screw 37.

In particular, the counterbore 40 is obtained on a front side of the bulge 35 being opposed to the supporting side of the humerus 11, and it defines a shoulder 42 in the bulge 35.

The counterbore 40 is eccentric, i.e., it has two centers, whose axes lie both on the plane of section VII highlighted in FIG. 7.

The first axis is coaxial with the seat 36 (axis Z), while a second axis T is coaxial with the counterbore 40. The eccentricity of the two axes Z and T is highlighted in FIG. 7 with E.

In other words, the counterbore 40 has a center positioned along an axis T being eccentric with respect to the axis Z of the seat 36.

Figure 15:
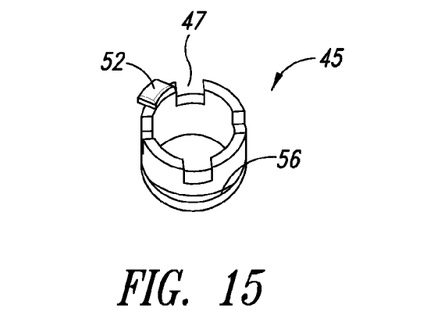
FIG. 15 shows a fixing ring of the screw of FIG. 9.
Figure 16:
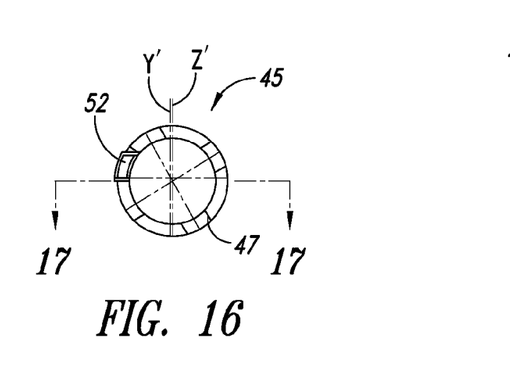
FIG. 16 shows a plan view of the fixing ring of FIG. 15.
Figure 17:
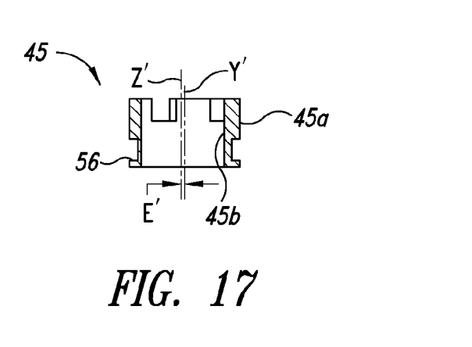
FIG. 17 shows a section of the fixing ring according to the line XVII-XVII of FIG. 16.

Moreover the clamping system comprises a ring 45 (FIGS. 2, 3, 4, 15, 16, 17), which is suitable to be positioned in the counterbore 40 abutting against the shoulder 42. As best illustrated in FIGS. 15-17, the ring 45 is eccentric, i.e., it comprises an outer surface 45a centered on an axis Y' and an inner surface 45b centered on an axis Z' being offset with respect to Y'. The eccentricity of the two axes Z' and Y' is highlighted on the plane of section VII and indicated with E' in FIG. 17.

It must be noted that the eccentricity E of the counterbore 40 and the eccentricity E' of the ring 45 may have the same or a different value.

In particular, the eccentric ring 45 is housed within the counterbore 40; so that the outer surface 45a is in contact with the counterbore 40, while the inner surface 45b is in contact with the smooth head 38 of the cephalic screw 37.

Moreover the smooth head 38 of the cephalic screw 37 is also in contact with the inner surface of the seat 36.

In order to obtain the desired clamping, the eccentric ring 45 serves as a wedge and to this purpose it is rotated around the axis Z' in order to wedge by rotation between the counterbore 40 and the cephalic screw 37, radially forcing the latter to press on a side thereof in the seat 36 within the bulge 35.

Figures 18, 19:
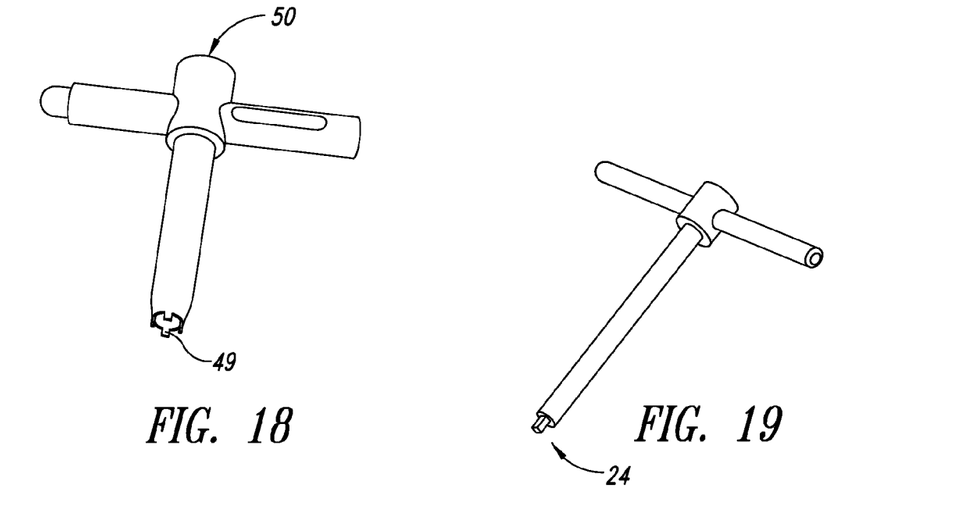
FIG. 18 shows a device to rotation-drive the fixing ring of FIG. 15.
FIG. 19 shows a device to screw down the screw of FIG. 9.

In order to perform the rotation, the eccentric ring 45 comprises driving grooves 47, cooperating with corresponding driving teeth 49 obtained on a corresponding tool, such as for example the tool 50 shown in FIG. 18.

Preferably, the rotation direction of the ring 45 is predetermined and it is indicated by an arrow obtained on the front side of the body 12.

Figures 3, 4:
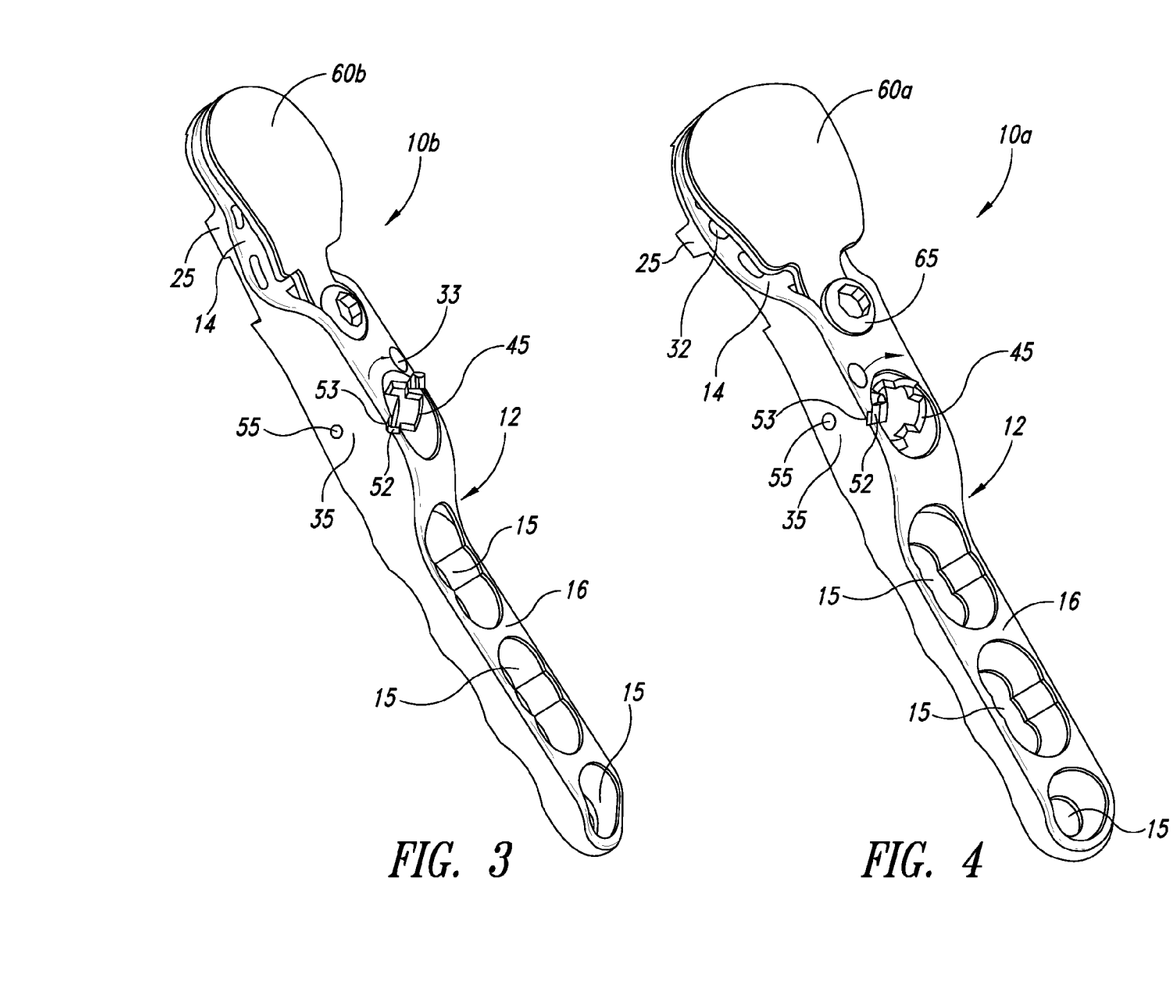
FIG. 3 shows an axonometric view of the device according to the invention for a left proximal humerus.
FIG. 4 shows an axonometric view of the device according to the invention for a right proximal humerus.

Preferably, in order to control the rotation, the eccentric ring 45 comprises a tooth 52 radially projecting from the edge of the ring 45 and positioning, after the rotation, in a limit stop notch 53 obtained on the bulge 35 next to the seat 36 (FIGS. 3 and 4).

In the solution being shown, in order to ensure the axial clamping of the eccentric ring 45, the device 10 also comprises a fastpin 54 (FIG. 2) suitable for insertion in a corresponding through hole 55 (FIG. 1) obtained in the bulge 35. The through hole 55 comes up in the counterbore 40.

In order to cooperate with the fastpin 54, the eccentric ring 45 has a circular groove 56 (FIG. 17) obtained on the outside on the cylindrical surface 45a thereof.

When the fastpin 54 is inserted in the hole 55, the groove 56 constrains the pin 54 further ensuring the clamping of the eccentric ring 45 to the body 12.

According to another feature of the present invention, in order to further reduce the compression of the whole device on the periosteous membrane, the body 12 is so shaped as to anatomically adhere to the bone shape.

To this purpose, as it can be noted from FIGS. 7 and 7A, the distal portion 16 extends parallel to said substantially vertical plane P, while the proximal portion 14 lies on the plane Y, forming an angle of about 150 with the plane P of the distal portion 16. This angle is indicated with β in FIG. 7.

Even more particularly, it must be noted that the proximal portion 14 is angled and it has a first portion 14a, i.e., the portion being adjacent to the bulge 35, which forms said angle β with the plane P of the distal portion 16, and a second portion 14b, i.e., the end portion being farthest from the bulge 35, which lies on a plane P' being substantially parallel to the plane P.

According to another feature of the invention, the proximal portion 14 has an anatomical profile being shaped to the humerus head 20 shape.

To this purpose, the proximal portion has a substantially rounded profile and it is also asymmetrical with respect to a median axis X passing along the whole body 12 (FIG. 5).

In particular, the proximal portion 14 has an expansion, or lobe 30, extending along an axis V being substantially orthogonal to the axis X (FIG. 5) and allowing the just-as-asymmetrical shape of the humerus head 20 to be completely wrapped.

As it can be observed in FIGS. 3, 4, 5 and 6, the anatomical shape of the proximal portion 14 inevitably involves a right and left design of the body 12.

The manufacturing of a device 10a (FIG. 4) according to the invention for a right humerus and of a device 10b (FIG. 3) according to the invention for a left humerus is thus provided.

The two devices 10a and 10b are specular with respect to each other and they only differ for the position of the expansion 30 which, in both devices, extends along the respective axis V in opposed directions.

For convenience of illustration, in the present description reference is indifferently made to either of the devices 10a, 10b for the right or left humerus respectively, it being understood that the only significant difference is the asymmetrical position of the expansion 30.

According to another feature of the invention, in order to favor the bone fragment compaction, the seats 32 for the insertion of wires 23 or threaded nails, are convergently angled towards the humerus head 20 (FIGS. 3 and 4).

Due to this feature, the threaded wires 23 inserted in the corresponding seat 32 are convergently angled in order to obtain a substantially convergent-nail-or-wire assembly having, in this specific case, a triangular base.

As it can be observed in the drawings, threaded wires or nails have a lower diameter than the screw one, and it corresponds to about 2.5 mm (0.46") and this allows a plurality of convergent nails to be positioned in the humerus head 20 without interfering with the screw 37.

Figure 2:
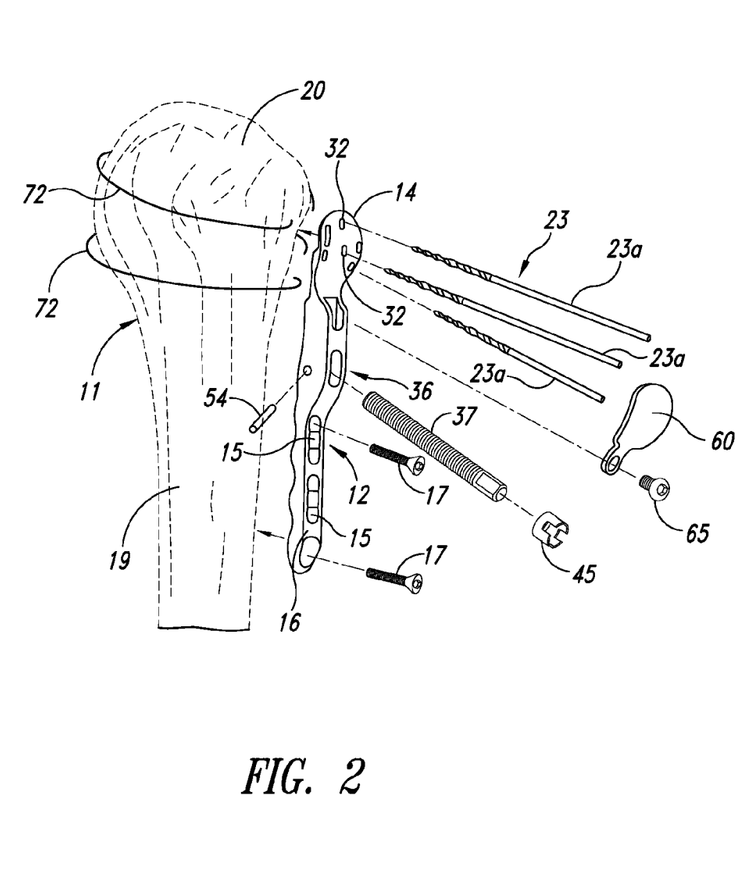
FIG. 2 shows an exploded view of a device according to an embodiment of the invention for the left humerus.

According to another feature of the present invention, in order to further favor the bone fragment compaction, the proximal portion 14 of the device 10 has a plurality of slots 70 (FIGS. 5 and 6), for example four, positioned on the periphery of the proximal portion 14, for the insertion of bent needles used to apply cerclage wires 72 of the humerus head 20 (FIGS. 1 and 2).

Preferably in correspondence with the slots 70, the device 10 has recesses 74 (FIG. 7A), or unburdenings, distributed on the edge of the portion 14. Recesses 74 favor a correct positioning of the cerclage wires 72 passing therethrough, reducing the contact-wear risk of cerclage wires 72 due to the friction.

Recesses 74 also define on the edge of the proximal portion 14 a plurality of appendixes 25 (FIGS. 7 and 7A), or feet, being turned towards the humerus 11 and allowing a "bridge" support of the device on the periosteous membrane. This support further favors the adhesion and a stable positioning.

To this purpose, according to another feature of the present invention, in order to further reduce the compression of the whole device 10 on the periosteous membrane, also the distal portion 16 and the bulge 35 have, on the side being turned towards the bone, a wavy profile 41 (FIG. 7A), allowing, similarly to feet 25, a "bridge" support of the device 10 on the periosteous membrane of the humerus 11 for the benefit of an improved stability.

According to another feature of the present invention, the distal portion 16 is further arranged to adjust the body 12 to the anatomical shape of the proximal humerus 11 and the position of the proximal portion 14 on the humerus head 20.

To this purpose it must be noted that two seats 15 for the fixing screws 17, particularly those obtained near the bulge 35, comprise a slot formed by three adjacent passages.

The passages have a spherical base and they allow the screw 17 to be selectively inserted in one of them. On the contrary the seat 15 obtained on the end of the distal portion 16 has a circular shape.

The selective insertion of the fixing screws 17 in either of the spherical passages allows the height of the body 12 to be adjusted along the humerus neck 19, thus keeping the fixing point unchanged.

According to an alternative embodiment, in the case of a body 12 having a higher length than the one being shown, the distal portion comprises six or seven seats for the fixing screws 17.

According to another feature of the present invention, the device 10 comprises a protection lid 60 (FIG. 1) being suitable to be put as a cover of the proximal portion 14.

Figure 11:
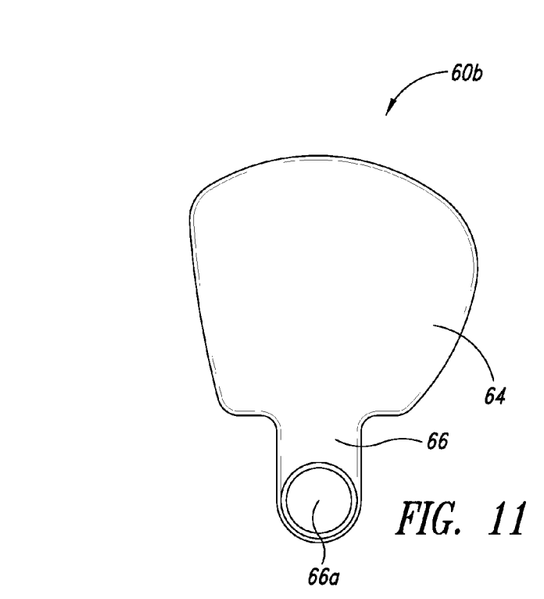
FIG. 11 shows a front view of a protection lid of the device of FIG. 3 for the left humerus.
Figure 12:
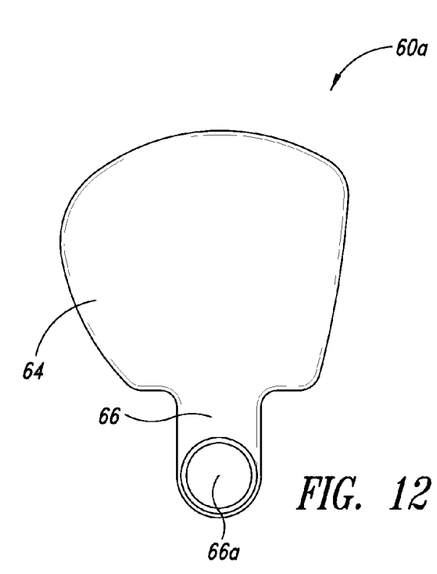
FIG. 12 shows a front view of a protection lid of the device of FIG. 4 for the right humerus.

In this case too, the anatomical shape of the proximal portion 14 involves a right design and a left design of the protection lid 60, which are specular to each other but not overlappable. In particular, FIG. 12 shows a protection lid 60a for a right humerus device, while FIG. 11 shows a protection lid 60b for a left humerus.

Similarly to the proximal portion 14, also the protection lid is asymmetrical and it comprises an expansion, or lobe, 64.

As it can be noted from the drawings, the protection lid 60 is concave, with a concavity corresponding to the proximal portion 14 one and it has on both faces, i.e., the one turned towards the body 12 and the front one turned outwardly, a smooth surface. This allows the lid 60 to simply rest on the ends of the threaded wires 23 projecting from the proximal portion 14, in order to protect the sheaths of muscular tissue and tendon sheaths from the friction with the ends of threaded wires 23.

Figure 13:
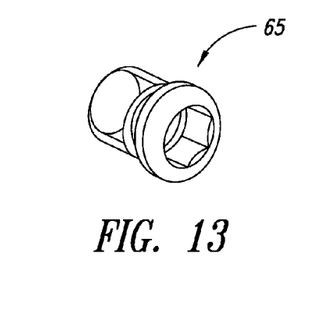
FIG. 13 shows a bolt to fix the protection lid of FIGS. 11 and 12.
Figure 14:
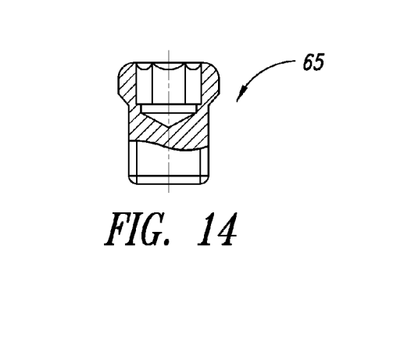
FIG. 14 shows a section of the fixing bolt of FIG. 13.

Preferably the protection lid 60 is fixed to the body 12 by means of a corresponding bolt 65 (FIG. 13).

To this purpose, the protection lid 60 comprises an appendix 66 having a through hole 66a for the insertion of the bolt 65.

The latter is screwed down in turn in a corresponding threaded hole 67 obtained through in the bulge 35 (FIG. 7).

In order to ensure a stability of the protection lid 60 on the body 12, the appendix 66 is inserted by pressure in a corresponding guide seat 68 (FIG. 5) obtained in the bulge 35 in correspondence with the threaded wire 67.

The guide seat 68 has, in the case of the solution being shown, a substantially U-shaped profile conjugated with the profile of the appendix 66.

The guide seat 68 allows the insertion of the appendix 66 to be driven up to the point wherein the hole 66a is aligned with the threaded hole 67 of the body 12 so as to favor a direct insertion of the bolt 65 and the screwing down thereof in the hole 67.

Preferably, the guide seat 68 extends flat in the bulge 35 according to a substantially parallel direction to the plane P whereon the distal portion 16 lies, as well as orthogonal to the screwing axis of the bolt 65 in the hole 67.

The main advantage of the device according to the present invention is that a stiff and integral structure between the body/plate bulge and the cephalic screw associated thereto.

This allows in the meantime the cephalic screw to be inserted in the seat obtained in the bulge and the seats obtained in the plate proximal portion to be kept free and unchanged for the threaded wire or nail insertion.

The bulge thus allows a stiff structure to be realized, although keeping the features and the spoon shape being typical of the plate unchanged.

In other words, the presence of the central bulge allows the screw to be fixed to the plate without affecting or changing the plate head portion and distal portion, totally preserving their own functions.

The head portion and the distal portion are thus left free for the insertion of threaded wires and fixing screws respectively.

Moreover, due to the substantially central arrangement thereof, the bulge does not influence at all the proximal portion shape, which preserves its blade-shaped concave anatomical shape shaped to the humerus head.

Moreover the proximal portion, preserving a lower thickness than the bulge, exerts a reduced pressure on the periosteous membrane with reduced risk of damage. To this purpose it must be noted that the bulge, being interposed between the proximal portion and the distal one, is not directly involved in the humerus head containment, thus allowing a reduced pressure to be kept thereon.

Another advantage of the present invention is that the device can be configured according to a plurality of modes being interchangeable between each other.

In a first configuration of the device according to the invention, suitable for example in the case of a fracture having a single fissure, only the cephalic screw is inserted in the plate in order to penetrate the humerus head and compress the two stumps formed by the fracture.

In a second embodiment, particularly suitable in the case of a fracture having a plurality of fragments, the cephalic screw is mounted on the plate in combination with the threaded wires or nails which are inserted in the plate proximal portion.

In a third configuration, particularly suitable in the case of a fracture having a plurality of fragments being positioned in different points of the humerus head, the cephalic screw is mounted on the plate in combination with cerclage wires.

In a forth configuration, useful for the most traumatic fractures, the cephalic screw is mounted on the plate in combination with both cerclage wires and threaded nails.

It obviously results that the combination of all these configurations allows a wide range of proximal humerus fractures to be covered.

The plurality of configurations of the device according to the invention thus allow a surgeon to choose, even during the intervention, the plate configuration being more suitable according to the traumatic situation being faced.

A further advantage of the present invention is the presence of the covering lid allowing the sheaths of muscular tissue and tendon sheaths from the friction of threaded wire heads.

Moreover the protection lid, due to the solid fixing obtained by the bolt, keeps a constant thrust on threaded wires increasing the stability of the latter with the plate.

Also the expedient to equip the plate with a guide seat for the assisted insertion of the protection lid appendix is particularly advantageous.

Due to the guide, the lid is easily inserted by the surgeon in the correct position. The insertion by pressure in the guide seat further increases the lid stability and the thrust thereof on threaded wire heads.

Obviously one skilled in the art, in order to meet contingent and specific requirements, can bring several changes and variations, all however falling in the scope of protection of the invention as defined by the following claims.

For example, in order to realize the cephalic screw clamping to the plate bulge, further alternative embodiments can be provided.

In a first alternative embodiment, not shown in the drawings, the eccentric ring, instead of being a separate element, is a body being integral with the stabilizing cephalic screw. In this case the ring is formed as a unique piece on the smooth head portion of the cephalic screw and it wedges by rotation between the cephalic screw and the counterbore in the same above-mentioned mode.

According to a further alternative embodiment, the clamping system comprises a dowel made of a compressible material, preferably made of a conveniently hard plastic material, being suitable to cooperate with the cephalic screw.

In particular, the dowel is positioned in the counterbore, in order to be interposed between the latter and the cephalic screw, when the latter is inserted and screwed down. The dowel is deformed by compression, thus determining the screw clamping.

A further clamping system is based on a forced coupling of a conic screw portion in a corresponding conic portion of the screw seat in the bulge.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A device for use in the treatment of proximal humerus fractures, having a substantially spoon-shaped body, or plate, comprising:
 a blade-like proximal portion intended to complement a portion of the humerus head and provided with at least one seat in which to insert a wire, a threaded nail, or a similar element to stabilize the fracture;
 a plate-like and elongate distal portion, intended to complement the humerus neck and provided with at least one seat in which to insert a screw or a similar element to fix the body to the humerus;
 a stabilizing screw;
a central bulge, or block, interposed between the proximal portion and the distal portion, having a thickness greater than either the proximal or the distal portions and including a central seat in which to insert a stabilizing screw intended to stabilize the humerus head;
 a cylindrical counterbore obtained in the central bulge and communicating with the central seat, said counterbore being eccentrically placed with respect to the central seat;
 wherein the device further comprises an eccentric ring comprising an outer cylindrical surface with a first axis, and an inner cylindrical surface with a second axis offset with respect to the first axis, an annular seat being defined between the counterbore and a head portion of the stabilizing screw when it is inserted in the central seat, the eccentric ring being within said annular seat embracing the head portion of the stabilizing screw, so that the ring inner surface is in contact with the head of the stabilizing screw and the ring outer surface is in contact with the counterbore, said eccentric ring being arranged to wedge by rotation between the counterbore and the stabilizing screw, radially forcing the latter to press on a side thereof in the seat within the bulge, so that the stabilizing screw is tightened to the bulge
 wherein the device further comprises a protection lid suitable to be put as a cover of the proximal portion;
 wherein the protection lid has a rounded profile being asymmetrical with respect to a median axis passing along the whole body and further comprises an expansion, or lobe;
 wherein the protection lid comprises an appendix wherein a hole is positioned for the insertion of a fixing bolt of the protection lid to the body;
 wherein the body comprises a guide seat to allow an assisted positioning of the appendix; and
 wherein the guide seat is obtained in the bulge 2. A device according to claim 1 wherein the central seat comprises a through hole in the central bulge having a longitudinal axis forming an angle with respect to a plane along which the distal portion lies.

3. A device according to claim 2 wherein the angle of the central seat is of about 135° with respect to the plane of the distal portion.

4. A device according to claim 1 wherein the central bulge has an overall thickness comprised between about 9 and 11 mm, the distal portion has an overall thickness comprised between about 4 and 5 mm and the proximal portion an overall thickness comprised between about 0.9 and 1.5 mm.

5. A device according to claim 4 wherein the thickness of the bulge corresponds to 10 mm, the thickness of the distal portion corresponds to 4.5 mm and the thickness of the proximal portion corresponds to 1.1 mm.

6. A device according to claim 1 wherein the stabilizing screw is a self-drilling screw suitable for insertion in the central seat of the central bulge.

7. A device according to claim 6 wherein the stabilizing screw has a diameter comprised between 5 and 7 mm.

8. A device according to claim 6 wherein the stabilizing screw is cannulated to allow the insertion of a guide wire.

9. A device according to claim 1 wherein the eccentric ring comprises a tooth, radially projecting from the edge of the ring and being suitable to position, after the rotation, in a stop limit groove obtained on the bulge next to the central seat.

10. A device according to claim 1 wherein the proximal portion substantially lies on a first plane forming an angle with a second plane whereon the distal portion lies.

11. A device according to claim 10 wherein the angle of inclination with respect to the second plane whereon the distal portion lies is of about 15°.

12. A device according to claim 1 wherein the proximal portion is angled and it has a first portion which lies on a first plane forming an angle with respect to a second plane whereon the distal portion lies, and a second portion which lies on a parallel plane being substantially parallel to the second plane whereon the distal portion lies.

13. A device according to claim 1 wherein the proximal portion has a rounded profile and is asymmetrical with respect to a median axis passing along the whole body.

14. A device according to claim 13 wherein the proximal portion has an expansion, or lobe, extending along an axis being substantially orthogonal to the median axis.

15. A device according to claim 1 wherein the proximal portion is concave with the concavity intended to be turned towards the humerus.

16. A device according to claim 1 wherein the distal portion and the bulge have a wavy profile on a side intended to be turned towards the humerus.

17. A device according to claim 1 wherein the seats within the proximal portion are convergently angled with respect to each other in order to obtain a substantially convergent-nail-or-wire assembly.

18. A device according to claim 1 wherein the proximal portion has more than one seat and the seats within the proximal portion are positioned according to a substantially triangular configuration in the proximal portion.

19. A device according to claim 1 wherein the body has a plurality of slots positioned on the periphery of the proximal portion, for the insertion of cerclage wires of the humerus head.

20. A device according to claim 19 wherein the proximal portion has a plurality of recesses, or unburdenings positioned in correspondence with the slots, and favoring a correct positioning of the cerclage wires.

21. A device according to claim 1 wherein the body comprises supporting feet obtained on an edge of the proximal portion on a side thereof intended to be turned towards the humerus.

22. A device according to claim 1 wherein the guide seat has a substantially U-shaped profile being conjugated to the one of the appendix.

23. A device according to claim 1 wherein the guide seat extends in the bulge according to a direction being substantially parallel to the plane wherein the distal portion of the body lies.

* * * * *